(12) United States Patent
Uchida

(10) Patent No.: US 7,488,831 B2
(45) Date of Patent: Feb. 10, 2009

(54) PROCESS FOR PRODUCING 5-HYDROXY-4-THIOMETHYLPYRAZOLE COMPOUND

(75) Inventor: Yukio Uchida, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 316 days.

(21) Appl. No.: 10/594,710

(22) PCT Filed: Mar. 31, 2005

(86) PCT No.: PCT/JP2005/006806

§ 371 (c)(1), (2), (4) Date: Sep. 28, 2006

(87) PCT Pub. No.: WO2005/095352

PCT Pub. Date: Oct. 13, 2005

(65) Prior Publication Data

US 2007/0185334 A1    Aug. 9, 2007

(30) Foreign Application Priority Data

Mar. 31, 2004   (JP) .......................... 2004-102963

(51) Int. Cl.
*C07D 231/14* (2006.01)
*A61K 31/415* (2006.01)

(52) U.S. Cl. .................................. 548/366.1; 514/407

(58) Field of Classification Search ................ 514/407; 548/366.1
See application file for complete search history.

(56) References Cited

FOREIGN PATENT DOCUMENTS

| WO | 2001/064651 A1 | | 9/2001 |
|---|---|---|---|
| WO | WO-01/64651 A1 | * | 9/2001 |
| WO | 2002/062770 A1 | | 8/2002 |
| WO | 2003/000686 A1 | | 1/2003 |
| WO | 2004/013106 A1 | | 2/2004 |
| WO | 2004/014138 A1 | | 2/2004 |

* cited by examiner

*Primary Examiner*—Rei-Tsang Shiao
*Assistant Examiner*—Janet L Coppins
(74) *Attorney, Agent, or Firm*—Arent Fox LLP

(57) ABSTRACT

A pyrazole compound represented by general formula (1) is reacted with a sulfur compound represented by general formula (2) in the presence of a base and formaldehyde, to thereby produce a 5-hydroxy-4-thiomethylpyrazole compound represented by general formula (3). The 5-hydroxy-4-thiomethylpyrazole compound may easily be produced in a good yield, by using such a process. Further, this process may easily provide the 5-hydroxy-4-thiomethylpyrazole compound under a mild condition in a single step, without using a special apparatus, an expensive catalyst, or a transition metal, etc. In addition, this process may be conducted substantially without producing a harmful waste which can be derived from a catalyst, etc., and therefore this process is friendly to the environment and industrially valuable.

6 Claims, No Drawings

PROCESS FOR PRODUCING 5-HYDROXY-4-THIOMETHYLPYRAZOLE COMPOUND

TECHNICAL FIELD

The present invention relates to a process for producing a 5-hydroxy-4-thiomethylpyrazole compound, which is useful as an intermediate in the production of pharmaceutical and agricultural chemicals.

BACKGROUND ART

The 5-hydroxy-4-thiomethylpyrazole compound obtained by the present invention is useful as an intermediate in the production of pharmaceutical and agricultural chemicals.

As for the process for producing a 4-thiomethylpyrazole compound, a method of reacting a 4-chloromethylpyrazole compound and a sulfur compound is known (see, Patent Document 1).

In order to obtain a 4-chloromethylpyrazole compound used as the raw material of this reaction, for example, after once synthesizing a pyrazole compound having a methyl group at the 4-position by a ring-closing reaction of corresponding β-ketoesters with hydrazines, the methyl group must be converted into a chloromethyl group by chlorination. Furthermore, for obtaining a 4-thiomethylpyrazole compound, this chloromethyl group must be reacted with an organic sulfur compound (see, Patent Document 1). However, this method is not satisfied as the industrial process for producing a 4-thiomethylpyrazole compound, because the reaction comprises multiple stages and the yield is not high due to difficulty in the selective monohalogenation of the methyl group at the 4-position of pyrazole.

As for the process for producing the 4-chloromethylpyrazole compound as the raw material in the above-described method, a method of directly chloromethylating a pyrazole compound unsubstituted at the 4-position is also known (see, Non-Patent Document 1). However, this method is problematic and hardly employable as the industrial production method, because the reaction is associated with by-production of a bis(chloromethyl) ether which is a carcinogenic substance.

Furthermore, a reaction of directly thiomethylating a pyrazole compound is not known.

(Patent Document 1) International Patent Publication WO2004/013106

(Non-Patent Document 1) *Journal of chemical Society*, pp. 1205-1208 (1955)

DISCLOSURE OF THE INVENTION

A method capable of solving those drawbacks in conventional techniques and simply and easily producing a 5-hydroxy-4-thiomethylpyrazole compound in a good yield has been demanded.

Under these circumstances, the present inventors have made intensive studies on the process for producing a 5-hydroxy-4-thiomethylpyrazole compound, as a result, it has been found that surprisingly, when a 5-hydroxypyrazole compound represented by formula (1) shown later is reacted with a sulfur compound represented by formula (2) shown later in the presence of a base and formaldehyde, a 5-hydroxy-4-thiomethylpyrazole compound represented by formula (3) shown later is produced. The present invention has been accomplished based on this finding.

According to the process of the present invention having such a constitution, a 5-hydroxy-4-thiomethylpyrazole compound represented by formula (3) can be produced from a 5-hydroxypyrazole compound represented by formula (1) in a good yield through a single step by a simple and easy operation method under mild conditions without using a special reaction apparatus or an expensive catalyst or transition metal. Moreover, in the process of the present invention, a harmful waste derived from a catalyst or transition metal is substantially not produced and therefore, this process is environment-friendly and has high industrial utility value.

In addition, according to the embodiment of using water as the solvent in the process of the present invention, a more environment-friendly process having a higher industrial utility value is provided.

EMBODIMENT OF THE INVENTION

The present invention includes, for example, the following embodiments [1] to [6].

[1] A process for producing a 5-hydroxy-4-thiomethylpyrazole compound, comprising: reacting a pyrazole represented by formula (1):

(Chemical Formula 1)

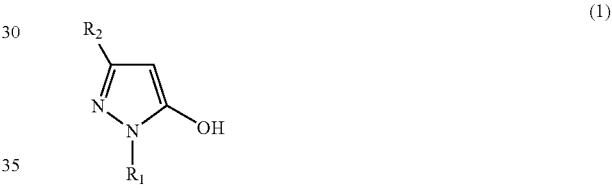

(wherein $R_1$ represents a hydrogen atom, an alkyl group, an aromatic hydrocarbon group capable of having a substituent, or a heterocyclic group capable of having a substituent, and $R_2$ represents an electron-withdrawing group) with a sulfur compound represented by formula (2):

(Chemical Formula 2)

$$X-S(O)_n-R_3 \quad (2)$$

(wherein X represents a hydrogen atom or a metal, $R_3$ represents an alkyl group, an aromatic hydrocarbon group capable of having a substituent, or a heterocyclic group capable of having a substituent, and n represents 0 or 2) in the presence of a base and formaldehyde-to produce a 5-hydroxy-4-thiomethylpyrazole compound represented by formula (3):

(Chemical Formula 3)

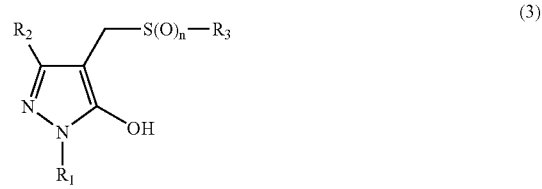

(wherein $R_1$, $R_2$, $R_3$ and n have the same meanings as above).

[2] The process for producing a 5-hydroxy-4-thiomethylpyrazole compound as described in [1], wherein n is 0.

[3] The process for producing a 5-hydroxy-4-thiomethylpyrazole compound as described in [1], wherein n is 2.

[4] The process for producing a 5-hydroxy-4-thiomethylpyrazole compound as described in any one of [1] to [3], wherein the electron-withdrawing group represented by $R_2$ is a trifluoromethyl group.

[5] The process for producing a 5-hydroxy-4-thiomethylpyrazole compound as described in any one of [1] to [3], wherein the electron-withdrawing group represented by $R_2$ is a cyano group.

[6] The process for producing a 5-hydroxy-4-thiomethylpyrazole compound as described in any one of [1] to [3], wherein the electron-withdrawing group represented by $R_2$ is an alkoxycarboxyl group, a carboxyl group or a metal salt thereof.

BEST MODE FOR CARRYING OUT THE INVENTION

The present invention is described in detail below. In the following, unless otherwise indicated, the "parts" and "%" denoting a quantitative ratio are on the mass basis.

(Process for producing 5-Hydroxy-4-Thiomethylpyrazole Compound)

The present invention relates to a process for producing a 5-hydroxy-4-thiomethylpyrazole compound represented by formula (3), comprising reacting a 5-hydroxypyrazole compound represented by formula (1) with a sulfur compound represented by formula (2) in the presence of a base and formaldehyde.

(Isomer)

The 5-hydroxypyrazole compound represented by formula (1) used as the raw material in the present invention and the 5-hydroxy-4-thiomethyl pyrazole compound represented by formula (3) as the product may be present in the form of a keto-enol tautomer. In the present invention, the raw material compound and the product are represented by a structure based on the enol form as in formulae (1) and (3), but in practice, the compositional ratio of the keto-enol tautomer sometimes varies depending on, for example, the solvent for dissolving the compound and even in such a case, the raw material or product in the process of the present invention includes both isomers of keto form/enol form.

(5-Hydroxypyrazole Compound)

The 5-hydroxypyrazole compound represented by formula (1) used as the raw material in the present invention is described below.

The method for obtaining the 5-hydroxypyrazole compound represented by formula (1) is not particularly limited. That is, any one method in the following examples may be used or other methods may also be used.

(Examples of Synthesis Method)

With respect to the synthesis method of the 5-hydroxypyrazole compound, for example, Hiroshi Yamanaka et al., *Hetero-Kan Kagobutsu no Kagaku* (*Chemistry of Heterocyclic Compounds*), Chap. 5, Kodansha Scientific (1988), and J. A. Joule and K. Mills, *Handbook of Heterocyclic Chemistry*, 2nd ed., Chap. 4.3.2.3, Pergamon (2000) may be referred to.

For example, a method of reacting a corresponding β-ketoester compound with a hydrazine, more specifically, a method where 1-methyl-5-hydroxy-3-trifluoromethylpyrazole can be synthesized in a yield of 49% by refluxing ethyl 4,4,4-trifluoroacetoacetate and methylhydrazine with a water solvent under heating for 2 hours, is reported in *Journal of Heterocyclic Chemistry*, Vol. 27, page 243 (1990).

Similarly, a method of reacting an oxaloacetic diester with a hydrazine to obtain a 3-(alkoxycarbonyl)-5-hydroxypyrazole compound, and a method of converting the alkoxycarbonyl group of the obtained compound into a cyano group are described in detail in Kokai (Japanese Unexamined Patent Publication) No. 10-287654.

Also, a method for obtaining a 3-cyano-5-hydroxypyrazole compound by a reaction of an α-cyanosuccinic acid with a diazonium salt is described in Kokoku (Japanese Examined Patent Publication) No. 51-33556.

(Substituent $R_1$)

As for formula (1) representing a 5-hydroxypyrazole compound which is the raw material compound in the process of the present invention, examples of the substituent represented by $R_1$ in formula (1) include the followings:

(1) a hydrogen atom;

(2) a linear or branched C1-C6 alkyl group having a carbon number of 1 to 6 (hereinafter, as for the carbon number, for example, when the carbon number is from 1 to 6, this is simply referred to as "C1-C6"), such as methyl group, ethyl group, n-propyl group, isopropyl group, n-butyl group, sec-butyl group, tert-butyl group, n-pentyl group and n-hexyl group;

(3) a monocyclic or condensed-ring aromatic hydrocarbon group with the number of atoms constituting the ring being from 6 to 14, preferably from 6 to 10, such as phenyl group and naphthyl group; the aromatic hydrocarbon group may have one or more substituent such as those in the following (3.1) to (3.21):

(3.1) a halogen atom such as bromo, chloro, fluoro and iodo, (3.2) a linear or branched C1-C6 alkyl group such as methyl group, ethyl group, n-propyl group, isopropyl group, n-butyl group, sec-butyl group, tert-butyl group, n-pentyl group and n-hexyl group, (3.3) a hydroxyl group, (3.4) a linear or branched C1-C6 alkoxy group such as methoxy group, ethoxy group, n-propoxy group and isopropoxy group, (3.5) a linear or branched C1-C6 hydroxyalkyl group such as hydroxymethyl group and 1-hydroxyethyl group, (3.6) a linear or branched (C1-C6 alkoxy)-(C1-C6 alkyl) group such as methoxymethyl group, 1-methoxyethyl group and 1-ethoxyethyl group, (3.7) a linear or branched C1-C6 haloalkyl group such as fluoromethyl group, difluoromethyl group and trifluoromethyl group, (3.8) a carboxyl group, (3.9) a metal salt of a carboxyl group, as represented by an alkali metal salt such as sodium salt, potassium salt and lithium salt, and an alkaline earth metal salt such as calcium salt, barium salt and magnesium salt, (3.10) a linear or branched (C1-C6 alkoxy)carbonyl group such as methoxycarbonyl group and ethoxycarbonyl group, (3.11) an arylcarbonyl group with the number of atoms constituting the ring being from 6 to 14, preferably from 6 to 10, such as benzoyl group and naphthoyl group, (3.12) a monocyclic or condensed-ring heteroarylcarbonyl group having from 1 to 4 heteroatoms which are at least one member selected from a nitrogen atom, an oxygen atom and a sulfur atom, with the number of atoms constituting the ring being from 5 to 14, preferably from 5 to 10, such as pyridylcarbonyl group, thienylcarbonyl group and furylcarbonyl group, (3.13) a nitro group,
(3.14) an amino group,
(3.15) a linear or branched mono-or di-(C1-C6 alkyl) amino group such as methylamino group, dimethylamino group, ethylamino group and diethylamino group,
(3.16) a linear or branched (C1-C6 alkyl)carbonylamino group such as acetylamino group, propionylamino group and butyrylamino group,
(3.17) a linear or branched hydroxycarbonyl(C1-C6 alkyl) group such as hydroxycarbonylmethyl group and 1-hydroxycarbonylethyl group,
(3.18) a linear or branched (C1-C6 alkoxy)carbonyl-(C1-C6 alkyl) group such as methoxycarbonylmethyl group, 1-methoxycarbonylethyl group and 1-ethoxycarbonylethyl group,
(3.19) a linear or branched aminocarbonyl-(C1-C6 alkyl) group such as aminocarbonylmethyl group and 1-aminocarbonylethyl group,
(3.20) a linear or branched (C1-C6 alkyl)aminocarbonyl-(C1-C6 alkyl) group such as methylaminocarbonylmethyl group, 1-methylaminocarbonylethyl group and 1-ethylaminocarbonylethyl group, and
(3.21) a cyano group;
(4) a monocyclic or condensed-ring aromatic heterocyclic group having from 1 to 4 heteroatoms which are at least one member selected from a nitrogen atom, an oxygen atom and a sulfur atom, with the number of atoms constituting the ring being from 5 to 14, preferably from 5 to 10, as represented by, for example, a furyl group, a benzofuryl group, a pyridyl group, a thienyl group, a benzothienyl group, an oxazolyl group, a benzoxazolyl group, a thiazolyl group, a benzothiazolyl group, an isooxazolyl group, a thiadiazolyl group, a pyrazyl group, a pyrimidinyl group, an indolyl group, a quinolinyl group, a pyrazolyl group, an imidazolyl group, a benzimidazolyl group, a triazolyl group and a triazinyl group; the aromatic heterocyclic group may have one or more substituent such as those in the following (4.1) to (4.19):
(4.1) a linear or branched C1-C6 alkyl group such as methyl group, ethyl group, n-propyl group, isopropyl group, n-butyl group, sec-butyl group, tert-butyl group, n-pentyl group and n-hexyl group,
(4.2) a hydroxyl group,
(4.3) a linear or branched C1-C6 alkoxy group such as methoxy group, ethoxy group, n-propoxy group and isopropoxy group,
(4.4) a linear or branched C1-C6 hydroxyalkyl group such as hydroxymethyl group and hydroxyethyl group,
(4.5) a linear or branched (C1-C6 alkoxy)-(C1-C6 alkyl) group such as methoxymethyl group, methoxyethyl group and ethoxyethyl group,
(4.6) a linear or branched C1-C6 haloalkyl group such as fluoromethyl group, difluoromethyl group and trifluoromethyl group,
(4.7) a carboxyl group,
(4.8) a metal salt of a carboxyl group, as represented by an alkali metal salt such as sodium salt, potassium salt and lithium salt, and an alkaline earth metal salt such as calcium salt, barium salt and magnesium salt,
(4.9) a linear or branched (C1-C6 alkoxy)carbonyl group such as methoxycarbonyl group and ethoxycarbonyl group,
(4.10) a halogen atom such as bromo, chloro, fluoro and iodo,
(4.11) a nitro group,
(4.12) an amino group, (4.13) a linear or branched mono- or di-(C1C6 alkyl)amino group such as methylamino group, dimethylamino group, ethylamino group and diethylamino group,
(4.14) a linear or branched (C1-C6 alkyl)carbonylamino group such as acetylamino group, propionylamino group and butyrylamino group,
(4.15) a cyano group,
(4.16) a formyl group,
(4.17) a linear or branched (C1-C6 alkyl)carbonyl group such as methylcarbonyl group and ethylcarbonyl group,
(4.18) an arylcarbonyl group with the number of atoms constituting the ring being from 6 to 14, preferably from 6 to 10, such as benzoyl group and naphthoyl group, and
(4.19) a monocyclic or condensed-ring heteroarylcarbonyl group having from 1 to 4 heteroatoms which are at least one member selected from a nitrogen atom, an oxygen atom and a sulfur atom, with the number of atoms constituting the ring being from 5 to 14, preferably from 5 to 10, such as pyridylcarbonyl group, thienylcarbonyl group and furylcarbonyl group; and
(5) a monocyclic or condensed-ring non-aromatic heterocyclic group having from 1 to 4 heteroatoms which are at least one member selected from a nitrogen atom, an oxygen atom and a sulfur atom, with the number of atoms constituting the ring being from 5 to 14, preferably from 5 to 10, as represented by, for example, a hydrofuryl group, a pyranyl group, a thioranyl group, a thianyl group, a pyrrolidinyl group, an indolinyl group, a piperidinyl group, an imidazolidinyl group and a piperazinyl group; the non-aromatic heterocyclic group may have one or more substituent such as those in the following (5.1) to (5.19):
(5.1) a linear or branched C1-C6 alkyl group such as methyl group, ethyl group, n-propyl group, isopropyl group, n-butyl group, sec-butyl group, tert-butyl group, n-pentyl group and n-hexyl group,
(5.2) a hydroxyl group,
(5.3) a linear or branched C1-C6 alkoxy group such as methoxy group, ethoxy group, n-propoxy group and isopropoxy group,
(5.4) a linear or branched C1-C6 hydroxyalkyl group such as hydroxymethyl group and hydroxyethyl group,
(5.5) a linear or branched (C1-C6 alkoxy)-(C1-C6 alkyl) group such as methoxymethyl group, methoxyethyl group and ethoxyethyl group,
(5.6) a linear or branched C1-C6 haloalkyl group such as fluoromethyl group, difluoromethyl group and trifluoromethyl group,
(5.7) a carboxyl group,
(5.8) a metal salt of a carboxyl group, as represented by an alkali metal salt such as sodium salt, potassium salt and lithium salt, and an alkaline earth metal salt such as calcium salt, barium salt and magnesium salt,
(5.9) a linear or branched (C1-C6 alkoxy)carbonyl group such as methoxycarbonyl group and ethoxycarbonyl group,
(5.10) a halogen atom such as bromo, chloro, fluoro and iodo,
(5.11) a nitro group,
(5.12) an amino group,
(5.13) a linear or branched mono- or di-(C1-C6 alkyl) amino group such as methylamino group, dimethylamino group, ethylamino group and diethylamino group,
(5.14) a linear or branched (C1-C6 alkyl)carbonylamino group such as acetylamino group, propionylamino group and butyrylamino group,
(5.15) a cyano group,
(5.16) a formyl group,
(5.17) a linear or branched (C1-C6 alkyl)carbonyl group such as methylcarbonyl group and ethylcarbonyl group, (5.18) an arylcarbonyl group with the number of atoms constituting the ring being from 6 to 14, preferably from 6 to 10, such as benzoyl group and naphthoyl group, and (5.19) a monocyclic or condensed-ring heteroarylcarbonyl group having from 1 to 4 heteroatoms which are at least one member selected from a nitrogen atom, an oxygen atom and a sulfur atom, with the number of atoms constituting the ring being from 5 to 14, preferably from 5 to 10, such as pyridylcarbonyl group, thienylcarbonyl group and furylcarbonyl group.

(Preferred Substituent $R_1$)

Among those described above, in view of easy availability, the followings are suitably usable as the substituent $R_1$.

A C1-C6 alkyl group as represented by methyl, and an aromatic hydrocarbon group with the number of atoms constituting the ring being from 6 to 14, as represented by phenyl are preferred, and a methyl group and a phenyl group are more preferred.

(Electron-Withdrawing Group $R_2$)

The electron-withdrawing group represented by $R_2$ in formula (1) means an atomic group capable of withdrawing an electron from the other party by the induction effect, an aromatic hydrocarbon group having such an atomic group, or an aromatic heterocyclic group having such an atomic group. Specific examples of the electron-withdrawing group $R_2$ include the followings:

(1) a linear or branched C1-C6 haloalkyl group such as difluoromethyl group and trifluoromethyl group; a carboxyl group, or a metal salt of a carboxyl group, as represented by an alkali metal salt such as sodium salt, potassium salt and lithium salt, and an alkaline earth metal salt such as calcium salt, barium salt and magnesium salt;

(2) a liner or branched (C1-C6 alkoxy)carbonyl group such as methoxycarbonyl group and ethoxycarbonyl group;

(3) a halogen atom such as bromo, chloro, fluoro and iodo; a nitro group; a formyl group;

(4) a linear or branched (C1-C6 alkyl)carbonyl group such as methylcarbonyl group (acetyl group) and ethylcarbonyl group;

(5) an arylcarbonyl group with the number of atoms constituting the ring being from 6 to 14, preferably from 6 to 10, such as benzoyl group and naphthoyl group;

(6) a monocyclic or condensed-ring heteroarylcarbonyl group having from 1 to 4 heteroatoms which are at least one member selected from a nitrogen atom, an oxygen atom and a sulfur atom, with the number of atoms constituting the ring being from 5 to 14, preferably from 5 to 10, such as pyridylcarbonyl group, thienylcarbonyl group and furylcarbonyl group;

(7) aminocarbonyl group, a linear or branched mono-or di-(C1-C6 alkyl)aminocarbonyl group such as methylaminocarbonyl group and dimethylaminocarbonyl group; a cyano group;

(8) an aromatic hydrocarbon group containing, as the substituent, one or more atomic group capable of withdrawing an electron from the other party by the induction effect, with the number of atoms constituting the ring being from 6 to 14, preferably from 6 to 10, such as chlorophenyl group (e.g., 2,4-dichlorophenyl), carboxyphenyl group and nitrophenyl group; and (9) a monocyclic or condensed-ring aromatic heterocyclic group containing, as the substituent, one or more atomic group capable of withdrawing an electron from the other party by the induction effect, and having from 1 to 4 heteroatoms which are at least one member selected from a nitrogen atom, an oxygen atom and a sulfur atom, with the number of atoms constituting the ring being from 5 to 14, preferably from 5 to 10, such as chlorofuryl group, chlorobenzofuryl group, chloropyridyl group, chlorothienyl group, carboxylbenzothienyl group, nitrooxazolyl group, cyanobenzooxazolyl group, chlorothiazolyl group, chlorobenzothiazolyl group, acetyl isooxazolyl group, benzoylthiadiazolyl group, chloropyrazyl group, chloropyrimidinyl group, chloroindolyl group, chloroquinolinyl group, aminocarbonylpyrazolyl group, methylaminocarbonylimidazolyl group, trifluoromethylbenzoimidazolyl group, methoxycarbonyltriazolyl group, and chlorotriazinyl group.

(Preferred Electron-Withdrawing Group $R_2$)

Among those described above, in view of stability under the reaction condition, that is, in the presence of a base, and eventual stability in the yield, the followings are suitably usable as the electron-withdrawing group $R_2$.

A C1-C6 haloalkyl group as represented by trifluoromethyl; an aromatic hydrocarbon group containing, as the substituent, one or more atomic group capable of withdrawing an electron from the other party by the induction effect, with the number of atoms constituting the ring being from 6 to 14, as represented by 2,4-dichlorophenyl; and a cyano group are preferred, and a trifluoromethyl group, 2,4-dichlorophenyl and a cyano group are more preferred.

(Preferred 5-Hydroxypyrazole Compound)

Accordingly, specific examples of the 5-hydroxypyrazole compound represented by formula (1) include 5-hydroxy-3-trifluoromethylpyrazole, 3-ethoxycarbonyl-5-hydroxypyrazole, 3-acetyl-5-hydroxypyrazole, 3-benzoyl-5-hydroxypyrazole, 5-hydroxy-3-(3-pyridylcarbonyl)pyrazole, 3-cyano-5-hydroxypyrazole, 5-hydroxy-1-methyl-3-trifluoromethylpyrazole, 3-ethoxycarbonyl-5-hydroxy-1-methylpyrazole, 3-chloro-5-hydroxy-1-methylpyrazole, 5-hydroxy-1-methyl-3-nitropyrazole, 5-hydroxy-1-methyl-3-(2-thienylcarbonyl)pyrazole, 5-hydroxy-1-methyl-3-(3-pyridylcarbonyl)pyrazole, 3-dimethylaminocarbonyl-5-hydroxy-1-methylpyrazole, 5-hydroxy-1-methyl-3-(4-trifuloromethylphenyl)pyrazole, 3-(4-ethoxycarbonylphenyl)-5-hydroxy-1-methylpyrazole, 3-(2,4-dichlorophenyl)-5-hydroxy-1-methylpyrazole, 3-(3,5-dinitrophenyl)-5-hydroxy-1-methylpyrazole, 3-(4-dimethylaminocarbonyl)-5-hydroxy-1-methylphenylpyrazole, 5-hydroxy-1-n-propyl-3-trifluoromethylpyrazole, 3-cyano-1-n-hexyl-5-hydroxypyrazole, 1-tert-butyl-5-hydroxy-3-trifluoromethylpyrazole, 1-tert-butyl-3-(4-carboxyphenyl)-5-hydroxypyrazole, 3-(4-acetylphenyl)-1-tert-butyl-5-hydroxypyrazole, 1-tert-butyl-3-(4-cyanophenyl)-5-hydroxypyrazole, 5-hydroxy-1-phenyl-3-trifluoromethylpyrazole, 3-cyano-5-hydroxy-1-phenylpyrazole, 1-(4-chlorophenyl)-3-ethoxycarbonyl-5-hydroxypyrazole, 3-ethoxycarbonyl-5-hydroxy-1-(2-methylphenyl)pyrazole, 3-ethoxycarbonyl-5-hydroxy-1-(2-methoxymethylphenyl)pyrazole, 1-(4-acetylphenyl)-3-ethoxycarbonyl-5-hydroxypyrazole, 3-ethoxycarbonyl-5-hydroxy-1-(3-nitrophenyl)pyrazole, 5-hydroxy-1-(2-methoxyphenyl)-3-trifluoromethylpyrazole, 5-hydroxy-3-trifluoromethyl-1-(4-trifluoromethylphenyl)pyrazole, 1-(4-ethoxycarbonylphenyl)-5-hydroxy-3-trifluoromethylpyrazole, 1-(4-dimethylaminophenyl)-5-hydroxy-3-trifluoromethylpyrazole, 1-(4-acetylaminophenyl)-5-hydroxy-3-trifluoromethylpyrazole, 1-(4-methoxycarbonylmethylphenyl)-5-hydroxy-3-trifluoromethylpyrazole, 1-(4-dimethylaminocarbonylmethylphenyl)-5-hydroxy-3-trifluoromethylpyrazole, 1-(4-cyanophenyl)-5-hydroxy-3-trifluoromethylpyrazole, 1-(2- naphthyl)-5-hydroxy-3-trifluoromethylpyrazole, 1-(2-benzothiazolyl)-5-hydroxy-3-trifluoromethylpyrazole, 5-hydroxy-1-(2-pyridyl)-3-trifluoromethylpyrazole and 5-hydroxy-1-(2-pyrimidyl)-3-trifluoromethylpyrazole.

(Sulfur Compound)

The sulfur compound represented by formula (2) is described below.

Examples of the substituent represented by $R_3$ in formula (2) include the followings:

(1) a linear or branched C1-C6 alkyl group such as methyl group, ethyl group, n-propyl group, isopropyl group, n-butyl group, sec-butyl group, tert-butyl group, n-pentyl group and n-hexyl group; a monocyclic or condensed-ring aromatic hydrocarbon group with the number of atoms constituting the ring being from 6 to 14, preferably from 6 to 10, such as phenyl group and naphthyl group (the aromatic hydrocarbon group may have one or more substituent, for example, a linear or branched C1-C6 alkyl group such as methyl group, ethyl group, n-propyl group, isopropyl group, n-butyl group, sec-butyl group, tert-butyl group, n-pentyl group and n-hexyl group, (2) a hydroxyl group, (3) a linear or branched C1-C6 alkoxy group such as methoxy group, ethoxy group, n-propoxy group and isopropoxy group, (4) a linear or branched C1-C6 hydroxyalkyl group such as hydroxymethyl group and hydroxyethyl group, (5) a linear or branched (C1-C6 alkoxy)-(C1-C6 alkyl) group such as methoxymethyl group, methoxyethyl group and ethoxyethyl group, (6) a linear or branched C1-C6 haloalkyl group such as fluoromethyl group, difluoromethyl group and trifluoromethyl group, a carboxyl group, a metal salt of a carboxyl group, as represented by an alkali metal salt such as sodium salt, potassium salt and lithium salt, and an alkaline earth metal salt such as calcium salt, barium salt and magnesium salt, (7) a linear or branched (C1-C6 alkoxy)carbonyl group such as methoxycarbonyl group and ethoxycarbonyl group, (8) a halogen atom such as bromo, chloro, fluoro and iodo, a nitro group, an amino group, (9) a linear or branched mono- or di-(C1-C6 alkyl)amino group such as methylamino group, dimethylamino group, ethylamino group and diethylamino group,

(10) a linear or branched C1-C6 alkylcarbonylamino group such as acetylamino group, propionylamino group and butyrylamino group, a cyano group, a formyl group,

(11) a linear or branched (C1-C6 alkyl)carbonyl group such as methylcarbonyl group and ethylcarbonyl group,

(12) an arylcarbonyl group with the number of atoms constituting the ring being from 6 to 14, preferably from 6to 10, such as benzoyl group and naphthoyl group, and

(13) a monocyclic or condensed-ring heteroarylcarbonyl group having from 1 to 4 heteroatoms which are at least one member selected from a nitrogen atom, an oxygen atom and a sulfur atom, with the number of atoms constituting the ring being from 5 to 14, preferably from 5 to 10, such as pyridylcarbonyl group, thienylcarbonyl group and furylcarbonyl group); and

(14) an aromatic or non-aromatic heterocyclic group including a monocyclic or condensed-ring aromatic heterocyclic group having from 1 to 4 heteroatoms which are at least one member selected from a nitrogen atom, an oxygen atom and a sulfur atom, with the number of atoms constituting the ring being from 5 to 14, preferably from 5 to 10, as represented by, for example, a furyl group, a benzofuryl group, a pyridyl group, a thienyl group, a benzothienyl group, an oxazolyl group, a benzoxazolyl group, a thiazolyl group, a benzothiazolyl group, an isooxazolyl group, a thiadiazolyl group, a pyrazyl group, a pyrimidinyl group, an indolyl group, a quinolinyl group, a pyrazolyl group, an imidazolyl group, a benzimidazolyl group, a triazolyl group and a triazinyl group (the aromatic heterocyclic group may have one or more substituent, for example, a linear or branched C1-C6 alkyl group such as methyl group, ethyl group, n-propyl group, isopropyl group, n-butyl group, sec-butyl group, tert-butyl group, n-pentyl group and n-hexyl group,

(15) a hydroxyl group,

(16) a linear or branched C1-C6 alkoxy group such as methoxy group, ethoxy group, n-propoxy group and isopropoxy group,

(17) a linear or branched C1-C6 hydroxyalkyl group such as hydroxymethyl group and hydroxyethyl group,

(18) a linear or branched (C1-C6 alkoxy)-(C1-C6 alkyl) group such as methoxymethyl group, methoxyethyl group and ethoxyethyl group,

(19) a linear or branched C1-C6 haloalkyl group such as fluoromethyl group, difluoromethyl group and trifluoromethyl group,

(20) a carboxyl group, or a metal salt of a carboxyl group, as represented by an alkali metal salt such as sodium salt, potassium salt and lithium salt, and an alkaline earth metal salt such as calcium salt, barium salt and magnesium salt,

(21) a linear or branched (C1-C6 alkoxy)carbonyl group such as methoxycarbonyl group and ethoxycarbonyl group,

(22) a halogen atom such as bromo, chloro, fluoro and iodo, a nitro group, an amino group,

(23) a linear or branched mono- or di-(C1-C6 alkyl)amino group such as methylamino group, dimethylamino group, ethylamino group and diethylamino group,

(24) a linear or branched (C1-C6 alkyl)carbonylamino group such as acetylamino group, propionylamino group and butyrylamino group, a cyano group, a formyl group,

(25) a linear or branched (C1-C6 alkyl)carbonyl group such as methylcarbonyl group and ethylcarbonyl group,

(26) an arylcarbonyl group with the number of atoms constituting the ring being from 6 to 14, preferably from 6 to 10, such as benzoyl group and naphthoyl group, and

(27) a monocyclic or condensed-ring heteroarylcarbonyl group having from 1 to 4 heteroatoms which are at least one member selected from a nitrogen atom, an oxygen atom and a sulfur atom, with the number of atoms constituting the ring being from 5 to 14, preferably from 5 to 10, such as pyridylcarbonyl group, thienylcarbonyl group and furylcarbonyl group), and a monocyclic or condensed-ring non-aromatic heterocyclic group having from 1 to 4 heteroatoms which are at least one member selected from a nitrogen atom, an oxygen atom and a sulfur atom, with the number of atoms constituting the ring being from 5 to 14, preferably from 5 to 10, as represented by, for example, a hydrofuryl group, a pyranyl group, a thioranyl group, a thianyl group, a pyrrolidinyl group, an indolinyl group, a piperidinyl group, an imidazolidinyl group and a piperazinyl group (the non-aromatic heterocyclic group may have one or more substituent, for example, a linear or branched C1-C6 alkyl group such as methyl group, ethyl group, n-propyl group, isopropyl group, n-butyl group, sec-butyl group, tert-butyl group, n-pentyl group and n-hexyl group, a hydroxyl group,

(28) a linear or branched C1-C6 alkoxy group such as methoxy group, ethoxy group, n-propoxy group and isopropoxy group,

(29) a linear or branched C1-C6 hydroxyalkyl group such as hydroxymethyl group and hydroxyethyl group, ( ) a linear or branched (C1-C6 alkoxy)-(C1-C6 alkyl) group such as methoxymethyl group, methoxyethyl group and ethoxyethyl group,

(30) a linear or branched C1-C6 haloalkyl group such as fluoromethyl group, difluoromethyl group and trifluoromethyl group, a carboxyl group, a metal salt of a carboxyl group, as represented by an alkali metal salt such as sodium salt, potassium salt and lithium salt, and an alkaline earth metal salt such as calcium salt, barium salt and magnesium salt,

(31) a linear or branched (C1-C6 alkoxy)carbonyl group such as methoxycarbonyl group and ethoxycarbonyl group,

(32) a halogen atom such as bromo, chloro, fluoro and iodo, a nitro group, an amino group,

(33) a linear or branched mono- or di-(C1-C6 alkyl)amino group such as methylamino group, dimethylamino group, ethylamino group and diethylamino group,

(34) a linear or branched (C1-C6 alkyl)carbonylamino group such as acetylamino group, propionylamino group and butyrylamino group, a cyano group, a formyl group,

(35) a linear or branched (C1-C6 alkyl)carbonyl group such as methylcarbonyl group and ethylcarbonyl group,

(36) an arylcarbonyl group with the number of atoms constituting the ring being from 6 to 14, preferably from 6 to 10, such as benzoyl group and naphthoyl group, and

(37) a monocyclic or condensed-ring heteroarylcarbonyl group having from 1 to 4 heteroatoms which are at least one member selected from a nitrogen atom, an oxygen atom and a sulfur atom, with the number of atoms constituting the ring being from 5 to 14, preferably from 5 to 10, such as pyridylcarbonyl group, thienylcarbonyl group and furylcarbonyl group).

(Group X)

X in formula (2) represents, for example, a hydrogen atom; or a metal atom as represented by, for example, an alkali metal such as sodium, potassium and lithium, and an alkaline earth metal such as magnesium and calcium.

In the case where n in formula (2) is 0, the compound is a thiol or a salt thereof, and when n is 2, the compound is a sulfinic acid or a salt thereof.

In the sulfur compound represented by formula (2) for use in the reaction, X may be a hydrogen atom or a metal salt of an alkali metal such as sodium, potassium and lithium, or an alkaline earth metal such as magnesium and calcium. Furthermore, in the case where the sulfur compound is a thiol (a compound when n in formula (2) is 0), a precursor capable of producing a thiol, as represented by isothiuronium salt or the like which can be easily prepared by a reaction of the corresponding alkyl halide with thiourea, may be hydrolyzed in the same reaction vessel, so that a thiol working out to the raw material in the reaction can be formed in the system and used.

(Specific Example of Sulfur Compound)

Accordingly, specific examples of the sulfur compound represented by formula (2) include sodium thiomethoxide, sodium thioethoxide, 2-butanethiol, thiophenol, 2-ethylthiophenol, 4-methoxythiophenol, 4-chlorothiophenol, 4-nitrothiophenol, 4-dimethylaminothiophenol, 4-cyanothiophenol, 4-acetylthiophenol, 2-mercaptopyridine, 2-mercaptobenzoxazole, 2-mercaptobenzothiazole, an isothiuronium salt as represented by n-hexyl thiocarboxamidine hydrochloride, benzyl thiocarboxamidine hydrochloride and [5,5-dimethyl(4,5-dihydroisooxazol-3-yl)]thiocarboxamidine hydrochloride, sodium benzenesulfinate and sodium p-toluenesulfinate.

(Reaction Method)

The method of reacting a 5-hydroxypyrazole compound represented by formula (1) with a sulfur compound represented by formula (2) to produce a 5-hydroxy-4-thiomethylpyrazole compound represented by formula (3) is described below.

(Formaldehyde)

The above-described reaction is performed in the presence of formaldehyde. The form of formaldehyde for use in this reaction is not particularly limited and formaldehyde in any form may be used, but use of an aqueous formaldehyde solution at a concentration of 35 to 50% as represented by 35% formalin easily available as a commercial product, or paraformaldehyde (a polymer of formaldehyde, which produces formaldehyde in the system by undergoing hydrolysis and therefore, is usable as a formaldehyde equivalent) is easy in view of operation and preferred.

(Amount Used)

The amount of formaldehyde used may be sufficient if it is an equivalent amount or more per equivalent of the raw material compound represented by formula (1), but the amount used is usually from 1.0 to 5.0 equivalents, preferably from 1.0 to 3.0 equivalents, per mol of the raw material compound represented by formula (1).

The amount used of the sulfur compound represented by formula (2) may be sufficient if it is an equivalent amount or more to the raw material compound of formula (1), but the amount used is usually from 1.0 to 2.0 equivalents, preferably from 1.0 to 1.2 equivalents, per mol of the raw material compound represented by formula (1).

(Base)

In the present invention, the reaction is performed in the presence of a base. Examples of the base for use in the reaction include the followings:

(1) an alkali metal hydride such as sodium hydride, potassium hydride and lithium hydride;

(2) an alkali metal such as sodium metal, potassium metal and lithium metal;

(3) an alkali metal hydroxide such as sodium hydroxide, potassium hydroxide and lithium hydroxide;

(4) an alkaline earth metal hydroxide such as barium hydroxide, magnesium hydroxide and calcium hydroxide;

(5) an alkali metal carbonate such as sodium carbonate, potassium carbonate, sodium hydrogencarbonate and potassium hydrogencarbonate;

(6) an inorganic base as represented by, for example, an alkaline earth metal oxide such as barium oxide, magnesium oxide and calcium oxide; and a metal alkoxide such as sodium methoxide, sodium ethoxide, potassium methoxide, potassium ethoxide and tert-butoxy potassium; and (7) an organic base as represented by, for example, an alkali metal such as butyllithium.

Among these, an alkali metal hydroxide and a metal alkoxide are preferred in view of availability, and an alkali metal hydroxide, particularly, sodium hydroxide, is more preferred, because the reaction can be performed with a water solvent and therefore, the load such as wastewater aftertreatment can be reduced.

(Amount of Base Used)

The amount of the base used may be any amount as long as it is large enough to allow for satisfactory progress of the reaction, but the amount used is, for example, from 1.0 to 20 mol, preferably from 1.5 to 10 mol, more preferably from 1.5 to 3.0 mol, per mol of the 5-hydroxypyrazole compound (raw material compound) represented by formula (1).

(Solvent)

The reaction of the present invention may be performed in the presence of a solvent, if desired.

The solvent usable for the reaction may be sufficient if it does not inhibit the reaction, and examples thereof include water; alcohols such as methanol and ethanol; aromatic hydrocarbons such as toluene, xylene and chlorobenzene; halogenated aliphatic hydrocarbons such as dichloromethane and chloroform; aprotic polar solvents such as dimethylformamide, dimethylacetamide, N-methylpyrrolidone, tetramethylurea, hexamethylphosphoric triamide (HMPA) and propylene carbonate; ether-based solvents such as diethyl ether, tetrahydrofuran and dioxane; and aliphatic hydrocarbons such as pentane and n-hexane. These solvents may be used individually or as a mixed solvent at an arbitrary mixing ratio. In view of solubility and reactivity of the base, the reaction is preferably performed by using water or alcohols, more preferably in water or methanol.

The amount of the solvent may be sufficient if it is large enough to allow for satisfactory stirring of the reaction system, but the amount thereof is usually from 0.05 to 10 L (liter), preferably from 0.5 to 2 L, per mol of the 5-hydroxypyrazole compound (raw material compound) represented by formula (1).

(Reaction Conditions)

The reaction temperature of this reaction may be, for example, from 0° C. to the reflux temperature of the solvent used, but the reaction is preferably performed at 20 to 50° C., particularly, at room temperature with stirring, because this is simple and a good yield is obtained.

The reaction time of this reaction is not particularly limited, but the reaction can be satisfactorily completed usually in the time from 1 to 10 hours.

According to this reaction, a 5-hydroxy-4-thiomethylpyrazole compound represented by formula (3) can be produced in a good yield by a simple and easy operation method under mild conditions. The obtained 5-hydroxy-4-thiomethylpyrazole compound represented by formula (3) is a compound useful as an intermediate raw material for pharmaceutical and agricultural chemicals.

EXAMPLES

The process for producing the compound of the present invention is specifically described below by referring to Examples, but the present invention is not limited to these Examples.

Reference Example 1

Synthesis of 5-hydroxy-1-methyl-3-trifluoromethylpyrazole

Ethyl 4,4,4-trifluoroacetoacetate (92.1 g (0.5 mol)) was dissolved in 60.1 g (1.0 mol) of acetic acid. The resulting solution was cooled to 10° C. or less with stirring, and 65.8 g (0.5 mol) of an aqueous 35% methylhydrazine solution was added dropwise thereto over 1 hour. After the dropwise addition, the solution was stirred at room temperature for 1 hour and subsequently at 80° C. for 5 hours. When the reaction was completed, the reaction solution was cooled to room temperature, and 150 mL (milliliter) of toluene, 600 mL of water and 48 g (1.2 mol) of sodium hydroxide were added thereto. After liquid separation, 154 g (1.5 mol) of 35% hydrochloric acid was added dropwise to the obtained aqueous layer, and the produced crystal was collected by filtration. The crystal was washed twice with 50 mL of water and dried by a hot air drier to obtain 71.8 g (yield: 86.5%) of the title compound as a pale yellow crystal.

LC-MS (EI): m/z=166 ($M^+$), melting point: 179-180° C.

Reference Example 2

Synthesis of 5-hydroxy-1-phenyl-3-trifluoromethylpyrazole

Ethyl 4,4,4-trifluoroacetoacetate (18.4 g (0.1 mol)) was dissolved in 12.0 g (0.2 mol) of acetic acid. The resulting solution was cooled to 10° C. or less with stirring, and 11.8 g (0.11 mol) of phenylhydrazine was added dropwise thereto over 0.5 hours. After the dropwise addition, the solution was stirred at room temperature for 1 hour and subsequently at 80° C. for 5 hours. When the reaction was completed, the reaction solution was cooled to room temperature, and 100 mL of water was added thereto. The produced crystal was collected by filtration, washed twice with 50 mL of water and dried by a hot air drier to obtain 22.3 g (yield: 98.0%) of the title compound as a pale yellow crystal.

LC-MS(EI): m/z=228 ($M^+$), melting point: 190-192° C.

Reference Example 3

Synthesis of 5-hydroxy-3-trifluoromethylpyrazole hydrochloride

Ethyl 4,4,4-trifluoroacetoacetate (18.4 g (0.1 mol)) was dissolved in 20 mL of ethanol. The resulting solution was cooled to 10° C. or less with stirring, and 6.0 g (0.12 mol) of hydrazine was added dropwise thereto over 0.5 hours. After the dropwise addition, the solution was stirred at room temperature for 1 hour and subsequently at the reflux temperature for 5 hours. When the reaction was completed, the reaction solution was cooled to room temperature, and 100 mL of water and 20.6 g (0.2 mol) of 35% hydrochloric acid were added thereto. The produced crystal was collected by filtration, washed twice with 10 mL of water and dried by a hot air drier to obtain 12.8 g (yield: 68.1%) of the title compound as a white crystal.

LC-MS(EI): m/z=152 ($M^+$).

Reference Example 4

Synthesis of 3-ethoxycarbonyl-5-hydroxy-1-methylpyrazole

Monosodium diethyl oxaloacetate (50.0 g (0.24 mol)) was suspended in 500 mL of ethanol, and 25 mL of acetic acid was added thereto. Subsequently, 15 g (0.33 mol) of 97% methylhydrazine was added dropwise thereto over 0.5 hours with stirring. After the dropwise addition, the solution was stirred at room temperature for 2 hours and then at the reflux temperature for 5 hours. The resulting solution was cooled, ethanol was removed by distillation under reduced pressure, and 200 mL of ethyl acetate and 100 mL of water were added to the residue. After liquid separation, the aqueous layer was re-extracted with 50 mL of ethyl acetate, and the combined ethyl acetate layer was washed with 50 mL of water and then with 50 mL of saturated brine. The obtained ethyl acetate layer was dried over anhydrous sodium sulfate, and the solvent was removed by distillation under reduced pressure. After adding 100 mL of water to the precipitated crystal, the crystal was collected by filtration, washed with 10 mL of water and dried by a hot air drier to obtain 29.2 g (yield: 71.8%) of the title compound as a pale yellow crystal.

LC-MS(EI): m/z=170 (M$^+$), 125 (base), melting point: 151° C.

Reference Example 5

Synthesis of 3-cyano-5-hydroxy-1-phenylpyrazole

Water (120 mL) and 15 mL of 35% hydrochloric acid were added to 5.6 g (0.06 mol) of aniline, and the mixture was dissolved. Subsequently, 24 mL of water having dissolved therein 4.2 g (0.06 mol) of sodium nitrite was added dropwise thereto with stirring under ice cooling to 0 to 5° C., and the resulting solution was stirred for 1 hour to prepare benzenediazonium chloride. An aqueous solution of this diazonium salt was added dropwise to a 120 mL pyridine solution containing 10.2 g (0.06 mol) of diethyl α-cyanosuccinate with stirring under ice cooling. After the dropwise addition, the solution was stirred under ice cooling for 1 hour and then at room temperature for 1 hour. When the reaction was completed, 240 mL of an aqueous 2% sodium hydroxide solution was added, followed by stirring for 2 hours. The obtained reaction solution was added dropwise to 240 mL of 35% hydrochloric acid under ice cooling, and the precipitated crystal was collected by filtration, washed with 10 mL of water and dried by a hot air drier to obtain 8.4 g of the crude crystal of the title compound as a red-brown crystal. This crude crystal was recrystallized from diethyl ether-petroleum ether and dried by a hot air drier to obtain 5.7 g (yield: 51.3%) of the title compound as a pale yellow crystal.

LC-MS(EI): m/z=185 (M$^+$), 125 (base), melting point: 190° C.

Reference Example 6

Synthesis of 3-(2,4-dichlorophenyl)-5-hydroxy-1-methylpyrazole

Potassium ethyl malonate (22.1 g (0.13 mol)) was suspended in 200 mL of ethyl acetate, and 29.14 g (0.29 mol) of triethylamine and 13.7 g (0.14 mol) of magnesium chloride were sequentially added thereto with stirring under ice cooling. The resulting suspension liquid was stirred at 40° C. for 6 hours and again ice-cooled, and 20.9 g (0.1 mol) of 2,4-dichlorobenzoyl chloride was added dropwise thereto over 1 hour while keeping the reaction solution at 10° C. or less. After the dropwise addition, the stirring was continued at room temperature for 12 hours. Subsequently, 200 mL of 5% hydrochloric acid was added dropwise to the reaction solution, and the organic layer was separated. The obtained organic layer was washed twice with 50 mL of water and then with 30 mL of saturated brine, and the solvent was removed by distillation under reduced pressure. To the residue obtained by the concentration, 100 mL of ethanol was added. The resulting solution was cooled to 10° C. or less with stirring, and 13.1 g (0.1 mol) of an aqueous 35% methylhydrazine solution was added dropwise thereto over 1 hour. After the dropwise addition, the solution was stirred at room temperature for 1 hour and then at 80° C. for 3 hours. When the reaction was completed, the reaction solution was cooled to room temperature, 300 mL of water was added, and the produced crystal was collected by filtration. The crystal was washed twice with 50 mL of water and dried by a hot air drier to obtain 12.3 g (yield: 50.2%) of the title compound as a white crystal. $^1$H-NMR value (300 MHz, CDCl$_3$): σ=7.53 (d; J=1.8 Hz, 1H), 7.2-7.4 (m, 2H), 5.68 (s, 1H), 3.54 (s, 3H) ppm.

LC-MS (EI): m/z=242 [(M−1)$^+$], melting point: 221-223° C.

Reference Example 7

Synthesis of 3-(3,5-dinitrophenyl)-5-hydroxy-1-methylpyrazole

Potassium ethyl malonate (11.0 g (0.07 mol)) was suspended in 100 mL of ethyl acetate, and 14.5 g (0.19 mol) of triethylamine and 6.9 g (0.08 mol) of magnesium chloride were sequentially added thereto with stirring under ice cooling. The resulting suspension liquid was stirred at 40° C. for 6 hours and again ice-cooled, and 11.5 g (0.05 mol) of 3,5-dinitrobenzoyl chloride was added dropwise thereto over 1 hour while keeping the reaction solution at 10° C. or less. After the dropwise addition, the stirring was continued at room temperature for 12 hours. Subsequently, 100 mL of 5% hydrochloric acid was added dropwise to the reaction solution, and the organic layer was separated. The obtained organic layer was washed twice with 50 mL of water and then with 30 mL of saturated brine, and the solvent was removed by distillation under reduced pressure. To the residue obtained by the concentration, 100 mL of ethanol was added, and 2.4 g (0.05 mol) of 97% methylhydrazine was then added dropwise at room temperature with stirring. After the dropwise addition, the solution was stirred at room temperature for 1 hour and subsequently at 80° C. for 3 hours. When the reaction was completed, the reaction solution was cooled to room temperature, 300 mL of water was added, and the produced crystal was collected by filtration. The crystal was washed twice with 50 mL of water, and the obtained crystal was recrystallized from 50% aqueous ethanol and dried by a hot air drier to obtain 4.2 g (yield: 30.2%) of the title compound as a red crystal.

$^1$H-NMR value (300 MHz, MeOH-d4): σ=8.90 (t; J=2.1 Hz, 1H), 8.85 (d; J=2.1 Hz, 2H), 4.60 (s, 1H), 3.73 (s, 3H), 3.3-3.4 (m, 1H) ppm.

LC-MS (EI): m/z=264 (M$^+$), melting point: 230-231° C.

Reference Example 8

Synthesis of 3-chloro-5,5-dimethyl-4,5-dihydroisooxazole

Ethanol (500 mL) and 63.0 g (0.75 mol) of sodium hydrogencarbonate were added and stirred at room temperature. After blowing 84.2 g (1.50 mol) of isobutene gas for 0.5 hours, the temperature was elevated to 70° C., and 131.3 g (0.5 mol) of a 40% isopropyl ether solution of dichloroformoxime was gradually added dropwise to the reaction solution, followed by stirring at the same temperature for 8 hours. The resulting reaction solution was allowed to cool to 25° C. or less and after removing inorganic solids by filtration, the residue was subjected to distillation under reduced pressure of 62° C./1.1 kPa to obtain 32.3 g (yield: 51%) of 3-chloro-4,5-dihydroisooxazole as a colorless transparent liquid.

$^1$H-NMR value (300 MHz, MeOH-d4): σ=2.88 (s, 2 H), 1.41 (s, 3H) ppm.

LC-MS (EI): m/z=133 (M$^+$), 118 (base), boiling point: 50° C./0.7 kPa.

Reference Example 9

Synthesis of [5,5-dimethyl(4,5-dihydroisooxazol-3-yl)]-thiocarboxamidine hydrochloride 35% Hydrochloric acid (4.17 g (0.04 mol)) was added to an ethanol 100 mL (0.51/mol) solution containing 16.8 g (0.2 mol) of thiourea, and 26.7 g (0.2 mol) of 3-chloro-5,5-dimethyl-4,5-dihydroisooxazole was added dropwise thereto over 1 hour with stirring at room temperature, followed by stirring at 30° C. for 3 hours. Subsequently, 100 mL of toluene was added to the reaction solution and when the solvent was removed by distillation under reduced pressure, 58.3 g of a white crystal was precipitated. Thereafter, 300 mL of isopropyl alcohol was added to the obtained crude crystal, and the mixture was heated until the crystal was dissolved, and then gradually cooled to obtain 38.5 g (yield: 92.0%) of the title compound as a white crystal.

$^1$H-NMR value (300 MHz, MeOH-d4): σ=4.84 (s, 3 H), 3.08 (s, 2H), 1.46 (s, 3H) ppm.

Melting point: 147° C.

Example 1

Synthesis of 5-hydroxy-1-methyl-4-methylthiomethyl-3-trifluoromethylpyrazole

5-Hydroxy-1-methyl-3-trifluoromethylpyrazole (1.7 g (10 mmol)) synthesized in Reference Example 1 and 0.6 g (15 mmol) of sodium hydroxide were dissolved in 10 mL of water. While stirring the resulting solution at room temperature, 1.7 g (20 mmol) of a 35% formalin solution was added dropwise thereto, followed by stirring at the same temperature for 1 hour. Furthermore, 7.1 g (10 mmol) of an aqueous 10% sodium thiomethoxide solution was added dropwise thereto at room temperature, and the obtained mixture was stirred for 6 hours. After the reaction, 5.0 g (50 mmol) of 35% hydrochloric acid was added dropwise thereto, and the precipitated crystal was collected by filtration, washed twice with 5 mL of water and dried by a hot air drier to obtain 1.6 g (yield: 72.7%) of the title compound as a pale yellow crystal. This crystal was recrystallized from water-methanol and obtained as a white crystal.

$^1$H-NMR value (300 MHz, MeOH-d4): σ=4.86 (br, 1H), 3.64 (s, 3H), 3.56 (s, 2H), 2.02 (s, 3H) ppm.

LC-MS (EI): m/z=226 (M$^+$), 179 (base), melting point: 123-124° C.

Example 2

Synthesis of [(5-hydroxy-1-methyl-3-trifluoromethylpyrazol-4-yl)-methylthio]benzene 5-Hydroxy-1-methyl-3-trifluoromethylpyrazole (1.7 g (10 mmol)) synthesized in Reference Example 1 and 0.6 g (15 mmol) of sodium hydroxide were dissolved in 10 mL of water. While stirring the resulting solution at room temperature, 1.7 g (20 mmol) of a 35% formalin solution was added dropwise thereto, followed by stirring at the same temperature for 1 hour. Furthermore, 11.0 g (10 mmol) of thiophenol was added dropwise thereto at room temperature, and the obtained mixture was stirred for 7 hours. After the reaction, 5.0 g (50 mmol) of 35% hydrochloric acid was added dropwise thereto, and the precipitated crystal was collected by filtration, washed twice with 5 mL of water and dried by a hot air drier to obtain 2.2 g (yield: 76.4%) of the title compound as a pale yellow crystal. This crystal was recrystallized from n-hexane-2-propanol and obtained as a white crystal.

$^1$H-NMR value (300 MHz, MeOH-d4): σ=7.1-7.3 (m, 5H), 4.86 (br, 1H), 3.99 (s, 2H), 3.61 (s, 3H).

LC-MS (EI): m/z=288 (M$^+$), 110 (base), melting point: 152° C.

Example 3

Synthesis of 3-[(5-hydroxy-1-methyl-3-trifluoromethylpyrazol-4-yl)-methylthio]-4,5-dihydro-5,5-dimethylisooxazole 5-Hydroxy-1-methyl-3-trifluoromethylpyrazole (1.7 g (10 mmol)) synthesized in Reference Example 1 and 1.6 g (40 mmol) of sodium hydroxide were dissolved in 10 mL of water. While stirring the resulting solution at room temperature, 1.7 g (20 mmol) of a 35% formalin solution was added dropwise thereto, followed by stirring at the same temperature for 1 hour. Furthermore, a water 10 mL solution containing 2.1 g (10 mmol) of [5,5-dimethyl(4,5-dihydroisooxazol-3-yl)]thiocarboxamidine hydrochloride was added dropwise thereto at room temperature, and the obtained mixture was stirred at the same temperature for 2 hours. After the reaction, 5.0 g (50 mmol) of 35% hydrochloric acid was added dropwise thereto, and the precipitated crystal was collected by filtration, washed twice with 5 mL of water and dried by a hot air drier to obtain 2.5 g (yield: 80.1%) of the title compound as a pale yellow crystal. This crystal was recrystallized from n-hexane-2-propanol and obtained as a white crystal.

$^1$H-NMR value (300 MHz, MeOH-d4): σ=4.88 (br, 1H), 4.08 (s, 2H), 3.64 (s, 3H), 2.91 (s, 2H), 1.39 (s, 6H) ppm.

LC-MS (EI): m/z=309 (M$^+$), 177 (base), melting point: 115-116° C.

Example 4

Synthesis of 3-[(5-hydroxy-1-methyl-3-trifluoromethylpyrazol-4-yl)-methylthio]-4,5-dihydro-5,5-dimethylisooxazole 5-Hydroxy-1-methyl-3-trifluoromethylpyrazole (1.7 g (10 mmol)) synthesized in Reference Example 1 and 6.0 g (30 mmol) of a methanol solution of 28% sodium methoxide were dissolved in 10 mL of methanol. While stirring the resulting solution at room temperature, 1.7 g of paraformaldehyde was charged thereto, followed by stirring at the same temperature for 1 hour. Furthermore, 2.1 g (10 mmol) of [5,5-dimethyl(4,5-dihydroisooxazol-3-yl)]thiocarboxamidine hydrochloride was charged thereto at room temperature, and the obtained mixture was stirred for 2 hours. After the reaction, 5.0 g (50 mmol) of 35% hydrochloric acid was added dropwise thereto, 10 mL of water was further added, and the precipitated crystal was collected by filtration, washed twice with 5 mL of water and dried by a hot air drier to obtain 2.6 g (yield: 84.1%) of the title compound as a pale yellow crystal. The $^1$H-NMR spectrum agreed with that of Example 3.

Example 5

Synthesis of 3-[(5-hydroxy-1-methyl-3-trifluoromethylpyrazol-4-yl)-methylthio]-4,5-dihydro-5,5-dimethylisooxazole The title compound (2.3 g (yield: 74.2%)) was obtained as a pale yellow crystal by the same operation as in Example 4 except for changing the base to 4.2 g (30 mmol) of potassium carbonate in the reaction of Example 4. The $^1$H-NMR spectrum agreed with that of Example 3.

Example 6 (Embodiment where the Electron-Withdrawing Group is a Trifluoromethyl Group)

Synthesis of 4-[(5-hydroxy-1-methyl-3-trifluoromethylpyrazol-4-yl)-methylsulfonyl]toluene 5-Hydroxy-1-methyl-3-trifluoromethylpyrazole (8.3 g (50 mmol)) synthesized in Reference Example 1 and 3.0 g (75 mmol) of sodium hydroxide were dissolved in 50 mL of water. While stirring the resulting solution at room temperature, 8.5 g (100 mmol) of a 35% formalin solution was added dropwise thereto, followed by stirring at the same temperature for 1 hour. Furthermore, 9.0 g (50 mmol) of sodium p-toluenesulfinate was charged thereto at room temperature, and the obtained mixture was stirred for 2 hours. After the reaction, 25.0 g (250 mmol) of 35% hydrochloric acid was added dropwise thereto, 100 mL of water was further added, and the precipitated crystal was collected by filtration, washed twice with 20 mL of water and dried by a hot air drier to obtain 14.0 g (yield: 83.8%) of the title compound as a white crystal.

$^1$H-NMR value (300 MHz, MeOH-d4): σ=7.62 (d; J=8.4 Hz, 2H), 7.39 (d; J=8.4 Hz, 2H), 4.85 (br, 1H), 4.32 (s, 2H), 3.63 (s, 3H), 2.44 (s, 3H) ppm.

LC-MS (EI): m/z=334 (M$^+$), 179 (base), melting point: 135° C.

Example 7

Synthesis of 4-[(5-hydroxy-1-methyl-3-trifluoromethylpyrazol-4-yl)-methylsulfonyl]toluene 5-Hydroxy-1-methyl-3-trifluoromethylpyrazole (1.7 g (10 mmol)) synthesized in Reference Example 1 and 0.6 g (15 mmol) of sodium hydroxide were dissolved in 10 mL of DMF. While stirring the resulting solution at room temperature, 1.7 g of paraformaldehyde was charged thereto, followed by stirring at the same temperature for 1 hour. Furthermore, 1.8 g (10 mmol) of sodium p-toluenesulfinate was charged thereto at room temperature, and the obtained mixture was stirred for 2 hours. After the reaction, 5.0 g (50 mmol) of 35% hydrochloric acid was added dropwise thereto, 10 mL of water was further added, and the precipitated crystal was collected by filtration, washed twice with 5 mL of water and dried by a hot air drier to obtain 3.0 g (yield: 88.2%) of the title compound as a white crystal. The $^1$H-NMR spectrum agreed with that of Example 6.

Example 8

Synthesis of 4-[(5-hydroxy-1-methyl-3-trifluoromethylpyrazol-4-yl)-methylsulfonyl]toluene 5-Hydroxy-1-methyl-3-trifluoromethylpyrazole (1.7 g (10 mmol)) synthesized in Reference Example 1 and 0.6 g (15 mmol) of sodium hydroxide were dissolved in 10 mL of toluene. While stirring the resulting solution at room temperature, 1.7 g of paraformaldehyde was charged thereto, followed by stirring at the same temperature for 24 hours. Furthermore, 1.8 g (10 mmol) of sodium p-toluenesulfinate was charged thereto at room temperature, and the obtained mixture was stirred for 8 hours. After the reaction, 5.0 g (50 mmol) of 35% hydrochloric acid was added dropwise thereto, 30 mL of water was further added, and the precipitated crystal was collected by filtration, washed twice with 5 mL of water and dried by a hot air drier to obtain 3.0 g (yield: 88.2%) of the title compound as a pale yellow crystal. The $^1$H-NMR spectrum agreed with that of Example 6.

Example 9

Synthesis of 3-[(5-hydroxy-1-phenyl-3-trifluoromethylpyrazol-4-yl)-methylthio]-4,5-dihydro-5,5-dimethylisooxazole 5-Hydroxy-1-phenyl-3-trifluoromethylpyrazole (2.3 g (10 mmol)) synthesized in Reference Example 2 and 0.6 g (15 mmol) of sodium hydroxide were dissolved in 10 mL of water. While stirring the resulting solution at room temperature, 1.7 g (20 mmol) of a 35% formalin solution was added dropwise thereto, followed by stirring at the same temperature for 1 hour (Reaction Solution 1). Separately, 2.1 g (10 mmol) of [5,5-dimethyl(4,5-dihydroisooxazol-3-yl)]thiocarboxamidine hydrochloride was added to a water 10 mL solution containing 1.2 g (30 mmol) of sodium hydroxide, followed by stirring for 1 hour (Reaction Solution 2). Reaction Solution 2 was added dropwise to Reaction Solution 1, and the obtained mixture was stirred for 2 hours. After the reaction, 6.0 g (60 mmol) of 35% hydrochloric acid was added dropwise thereto, and the toluene layer obtained from an extraction operation performed twice with 20 mL of toluene was washed with 10 mL of water and then with 10 mL of saturated brine and dried over anhydrous sodium sulfate. Thereafter, toluene was removed by distillation under reduced pressure to obtain 3.3 g (yield: 89.2%) of the title compound as a viscous material. This viscous material was left standing at room temperature for 2 days and thereby crystallized.

$^1$H-NMR value (300 MHz, MeOH-d4): σ=7.3-7.7 (m, 4H), 4.90 (br, 1H), 4.16 (s, 2H), 2.92 (s, 2H), 1.37 (s, 6H) ppm.

Melting point: 89-92° C.

Example 10

Synthesis of 4-[(5-hydroxy-1-phenyl-3-trifluoromethylpyrazol-4-yl)-methylsulfonyl]benzene 5-Hydroxy-1-phenyl-3-trifluoromethylpyrazole (2.3 g (10 mmol)) synthesized in Reference Example 2 and 0.6 g (15 mmol) of sodium hydroxide were dissolved in 10 mL of water. While stirring the resulting solution at room temperature, 1.7 g (20 mmol) of a 35% formalin solution was added dropwise thereto, followed by stirring at the same temperature for 1 hour. Subsequently, 1.6 g (10 mmol) of sodium benzenesulfinate was charged thereto at room temperature, and the obtained mixture was stirred for 2 hours. After the reaction, 6.0 g (60 mmol) of 35% hydrochloric acid was added dropwise thereto, and the toluene layer obtained from an extraction operation performed twice with 20 mL of toluene was washed with 10 mL of water and then with 10 mL of saturated brine and dried over anhydrous sodium sulfate. Thereafter, toluene was removed by distillation under reduced pressure to obtain 3.4 g (yield: 88.1%) of the title compound as a viscous material. This viscous material was left standing at room temperature for 2 days and thereby crystallized.

$^1$H-NMR value (300 MHz, MeOH-d4): σ=7.3-7.9 (m; 10 H), 4.91 (br, 1H), 4.44 (s, 2H), 3.63 (s, 3H), 2.44 (s, 3H) ppm.

Melting point: 122-123° C.

Example 11

Synthesis of 3-[(5-hydroxy-3-trifluoromethylpyrazol-4-yl)-methylthio]-4,5-dihydro-5,5-dimethyl-isooxazole 5-Hydroxy-3-trifluoromethylpyrazole hydrochloride (1.9 g (10 mmol)) synthesized in Reference Example 3 and 1.2 g (30 mmol) of sodium hydroxide were dissolved in 10 mL of water. While stirring the resulting solution at room temperature, 1.7 g (20 mmol) of a 35% formalin solution was added dropwise thereto, followed by stirring at the same temperature for 1 hour (Reaction Solution 1). Separately, 2.1 g (10 mmol) of [5,5-dimethyl(4,5-dihydroisooxazol-3-yl)]thiocarboxamidine hydrochloride was added to a water 10 mL solution containing 1.2 g (30 mmol) of sodium hydroxide, followed by stirring for 1 hour (Reaction Solution 2). (Reaction Solution 2) was added dropwise to (Reaction Solution 1), and the obtained mixture was stirred for 2 hours. After the reaction, 6.0 g (60 mmol) of 35% hydrochloric acid was added dropwise thereto, and sodium hydrogencarbonate was then added carefully so that the reaction solution could have a pH of 7. The toluene layer obtained from an extraction operation performed twice with 20 mL of ethyl acetate was washed with 10 mL of water and then with 10 mL of saturated brine and dried over anhydrous sodium sulfate. Thereafter, ethyl acetate was removed by distillation under reduced pressure to obtain 2.4 g (yield: 81.3%) of the title compound as a viscous material. This viscous material was left standing at room temperature for 2 days and thereby crystallized.

$^1$H-NMR value (300 MHz, MeOH-d4): σ=5.35 (s; 1H), 4.86 (br, 1H), 4.10 (s, 2H), 2.92 (s, 2H), 1.39 (s, 6H) ppm.

LC-MS (EI): m/z=320 (M$^+$), 163 (base), melting point: 131-133° C.

Example 12

Synthesis of 3-[(5-hydroxy-3-trifluoromethylpyrazol-4-yl)-methylsulfonyl]toluene 5-Hydroxy-3-trifluoromethylpyrazole hydrochloride (1.9 g (10 mmol)) synthesized in Reference Example 3 and 1.2 g (30 mmol) of sodium hydroxide were dissolved in 10 mL of water. While stirring the resulting solution at room temperature, 1.7 g (20 mmol) of a 35% formalin solution was added dropwise thereto, followed by stirring at the same temperature for 1 hour. Subsequently, 1.8 g (10 mmol) of sodium p-toluenesulfinate was charged thereto at room temperature, and the obtained mixture was stirred for 2 hours. After the reaction, 5.0 g (50 mmol) of 35% hydrochloric acid was added dropwise thereto, 20 mL of water was further added, and the precipitated crystal was collected by filtration, washed twice with 10 mL of water and dried by a hot air drier to obtain 2.67 g (yield: 83.2%) of the title compound as a pale yellow crystal.

$^1$H-NMR value (300 MHz, MeOH-d4): σ=7.62 (d; J=8.1 Hz, 2H), 7.37 (d; J=8.1 Hz, 2H), 5.34 (s; 1H), 4.88 (s, 1H), 4.34(s, 2H), 2.43(s, 3H) ppm.

LC-MS (EI): m/z=295 (M$^+$), 163 (base), melting point: 130-133° C.

Example 13

Synthesis of 4-[(3-cyano-5-hydroxy-1-phenylpyrazol-4-yl)-methylsulfonyl]toluene

3-Cyano-5-hydroxy-1-phenylpyrazole (1.8 g (10 mmol)) synthesized in Reference Example 5 and 0.6 g (15 mmol) of sodium hydroxide were dissolved in 10 mL of water. While stirring the resulting solution at room temperature, 1.7 g (20 mmol) of a 35% formalin solution was added dropwise thereto, followed by stirring at the same temperature for 1 hour. Subsequently, 1.8 g (10 mmol) of sodium p-toluenesulfinate was charged thereto at room temperature, and the obtained mixture was stirred for 2 hours. After the reaction, 5.0 g (50 mmol) of 35% hydrochloric acid was added dropwise thereto, 20 mL of water was further added, and the precipitated crystal was collected by filtration, washed twice with 20 mL of water and dried by a hot air drier to obtain 3.0 g (yield: 85.7%) of the title compound as a pale yellow crystal.

$^1$H-NMR value (300 MHz, MeOH-d4): (σ=7.4-7.7 (m; 9H), 4.86 (s, 1H), 4.40 (s, 2H), 2.46 (s, 3H) ppm.

LC-MS (EI): m/z=353 (M$^+$), 197 (base), melting point: 214° C.

Example 14

Synthesis of 4-[(3-carboxy-5-hydroxy-1-phenylpyrazol-4-yl)-methylsulfonyl]toluene 5-Hydroxy-1-methyl-3-ethoxycarbonylpyrazole (1.7 g (10 mmol)) synthesized in Reference Example 4 and 1.2 g (30 mmol) of sodium hydroxide were dissolved in 20 mL of water. While stirring the resulting solution at room temperature, 1.7 g (20 mmol) of a 35% formalin solution was added dropwise thereto, followed by stirring at the same temperature for 1 hour. Subsequently, 1.8 g (10 mmol) of sodium p-toluenesulfinate was charged thereto at room temperature, and the obtained mixture was stirred for 2 hours. After the reaction, 5.0 g (50 mmol) of 35% hydrochloric acid was added dropwise thereto, 30 mL of water was further added, and the precipitated crystal was collected by filtration, washed twice with 20 mL of water and dried by a hot air drier to obtain 2.6 g (yield: 82.9%) of the title compound as a white crystal.

$^1$H-NMR value (300 MHz, MeOH-d4): σ=7.52 (d; J=8.1 Hz, 2H), 7.33 (d; J=8.1 Hz, 2H), 4.85 (s, 2H), 4.61 (s, 2H), 3.65 (s, 3H), 2.42 (s, 3H) ppm.

LC-MS (EI): m/z=310 (M$^+$), 155 (base), melting point: 228° C.

Example 15

Synthesis of 4-{[3-(2,4-dichlorophenyl)-5-hydroxy-1-methylpyrazol-4-yl]-methylsulfonyl}toluene 3-(2,4-Dichlorophenyl)-5-hydroxy-1-methylpyrazole (1.3 g (5 mmol)) synthesized in Reference Example 6 and 0.3 g (7.5 mmol) of sodium hydroxide were dissolved in 5 mL of ethanol. While stirring the resulting solution at room temperature, 1.0 g (11 mmol) of a 35% formalin solution was added dropwise thereto, followed by stirring at the same temperature for 1 hour. Subsequently, 0.9 g (5 mmol) of sodium p-toluenesulfinate was charged thereto at room temperature, and the obtained mixture was stirred for 2 hours. After the reaction, 2.5 g (25 mmol) of 35% hydrochloric acid was added dropwise thereto, 15 mL of water was further added, and the precipitated crystal was collected by filtration, washed twice with 10 mL of water and dried by a hot air drier to obtain 2.1 g (yield: 90.3%) of the title compound as a pale yellow crystal.

$^1$H-NMR value (300 MHz, CDCl$_3$): σ=7.0-7.4 (m, 7H), 4.24 (S, 2H), 3.69 (s, 3H), 3.50 (br, 1H), 2.43 (s, 3H) ppm.

LC-MS (EI): m/z=410 [(M−1)$^+$], 255 (base), melting point: 209° C.

Example 16

Synthesis of 4-{[3-(3,5-dinitrophenyl)-5-hydroxy-1-methylpyrazol-4-yl]-methylsulfonyl}toluene 3-(3,5-Dinitrophenyl)-5-hydroxy-1-methylpyrazole (0.65 g (2.5 mmol)) synthesized in Reference Example 4 and 0.15 g (3.8 mmol) of sodium hydroxide were dissolved in 5 mL of ethanol. While stirring the resulting solution at room temperature, 0.5 g (5.5 mmol) of a 35% formalin solution was added dropwise thereto, followed by stirring at the same temperature for 1 hour. Subsequently, 0.45 g (2.5 mmol) of sodium p-toluenesulfinate was charged thereto at room temperature, and the obtained mixture was stirred for 2 hours. After the reaction, 2.5 g (25 mmol) of 35% hydrochloric acid was added dropwise thereto, 15 mL of water was further added, and the precipitated crystal was collected by filtration, washed twice with 10 mL of water and dried by a hot air drier to obtain 0.9 g (yield: 89.3%) of the title compound as a brown crystal.

$^1$H-NMR value (300 MHz, CDCl$_3$): σ=8.88 (t; J=2.1 Hz, 1H), 8.52 (d; J=1.8 Hz, 2H), 7.55 (d; J=8.1 Hz, 2H), 7.16 (d; J=8.1 Hz, 2H), 4.43 (s, 2H), 3.85 (br, 1H), 3.76 (s, 3H), 2.31 (s, 3H) ppm.

LC-MS (EI): m/z=432 (M$^+$), 276 (base), melting point: 192-194° C.

INDUSTRIAL APPLICABILITY

A novel industrial process for producing a 5-hydroxy-4-thiomethylpyrazole compound is provided. According to the process of the present invention, a 5-hydroxy-4-thiomethylpyrazole compound is produced from a 5-hydroxypyrazole compound represented by formula (1) in a good yield through a single step by a simple and easy operation method under mild conditions without using a special reaction apparatus or an expensive catalyst or transition metal. Moreover, a harmful waste derived from a catalyst or transition metal is substantially not produced and therefore, this process is environment-friendly and has high industrial utility value.

In addition, according to the embodiment of using water as the solvent, a more environment-friendly process having a higher industrial utility value is provided.

The invention claimed is:

1. A process for producing a 5-hydroxy-4-thiomethylpyrazole compound, comprising: reacting a pyrazole represented by formula (1):

(Chemical Formula 1)

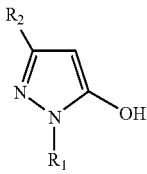

(1)

(wherein R$_1$ represents a hydrogen atom, an alkyl group, an aromatic hydrocarbon group capable of having a substituent, or a heterocyclic group capable of having a substituent, and R$_2$ represents an electron-withdrawing group), with a sulfur compound represented by the following formula (2):

(Chemical Formula 2)

$$X\text{—}S(O)_n\text{—}R_3 \tag{2}$$

(wherein X represents a hydrogen atom or a metal, R$_3$ represents an alkyl group, an aromatic hydrocarbon group capable of having a substituent, or a heterocyclic group capable of having a substituent, and n represents 0 or 2) in the presence of a base and formaldehyde, to thereby produce a 5-hydroxy-4-thiomethylpyrazole compound represented by the following formula (3):

(Chemical Formula 3)

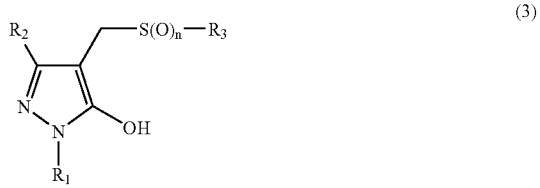

(3)

(wherein R$_1$, R$_2$, R$_3$ and n have the same meanings as those described above).

2. The process for producing a 5-hydroxy-4-thiomethylpyrazole compound according to claim 1, wherein n is 0.

3. The process for producing a 5-hydroxy-4-thiomethylpyrazole compound according to claim 1, wherein n is 2.

4. The process for producing a 5-hydroxy-4-thiomethylpyrazole compound according to any one of claims 1 to 3, wherein the electron-withdrawing group represented by R$_2$ is a trifluoromethyl group.

5. The process for producing a 5-hydroxy-4-thiomethylpyrazole compound according to any one of claims 1 to 3, wherein the electron-withdrawing group represented by R$_2$ is a cyano group.

6. The process for producing a 5-hydroxy-4-thiomethylpyrazole compound according to any one of claims 1 to 3, wherein the electron-withdrawing group represented by R$_2$ is an alkoxycarboxyl group, a carboxyl group or a metal salt thereof.

\* \* \* \* \*